US007734075B2

(12) United States Patent
Sun et al.

(10) Patent No.: US 7,734,075 B2
(45) Date of Patent: Jun. 8, 2010

(54) CONTRAST-INVARIANT REGISTRATION OF CARDIAC AND RENAL MAGNETIC RESONANCE PERFUSION IMAGES

(75) Inventors: Ying Sun, Plainsboro, NJ (US); Marie-Pierre Jolly, Hillsborough, NJ (US); Jose M. F. Moura, Pittsburgh, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1489 days.

(21) Appl. No.: 11/078,035

(22) Filed: Mar. 11, 2005

(65) Prior Publication Data

US 2005/0240099 A1    Oct. 27, 2005
US 2009/0240136 A9    Sep. 24, 2009

Related U.S. Application Data

(63) Continuation-in-part of application No. 09/970,552, filed on Oct. 4, 2001, now Pat. No. 6,961,454.

(60) Provisional application No. 60/553,216, filed on Mar. 15, 2004.

(51) Int. Cl.
*G06K 9/00* (2006.01)
*A61B 5/05* (2006.01)

(52) U.S. Cl. ..................... 382/128; 600/410

(58) Field of Classification Search ......... 382/128–134, 382/164, 171, 173, 179, 103, 100, 181, 194, 382/199, 158; 600/410, 425, 411; 128/922; 345/418, 421; 356/38, 39, 12; 378/28, 41, 378/46, 90; 377/10, 11; 340/907, 933–937
See application file for complete search history.

(56) References Cited

U.S. PATENT DOCUMENTS

| | | | | |
|---|---|---|---|---|
| 6,075,905 A | * | 6/2000 | Herman et al. | 382/284 |
| 6,757,423 B1 | * | 6/2004 | Amini | 382/154 |
| 6,961,454 B2 | * | 11/2005 | Jolly | 382/131 |
| 2002/0103429 A1 | * | 8/2002 | deCharms | 600/410 |
| 2003/0035573 A1 | * | 2/2003 | Duta et al. | 382/128 |
| 2003/0069494 A1 | * | 4/2003 | Jolly | 600/410 |

OTHER PUBLICATIONS

Learning-based object detection in cardiac MR images, Duta, N.; Jain, A.K.; Dubuisson-Jolly, M.-P.;Computer Vision, 1999, vol. 2, Sep. 20-27, 1999 pp. 1210-1216 vol. 2, Digital Object Identifier 10.1109/ICCV.1999.790418.*
Curve registration, J. O. Ramsay and Xiaochun Li, McGill University, Montreal, Canada 1998 Royal Statistical Society 1360-7412/98/60351.*

* cited by examiner

*Primary Examiner*—Samir A Ahmed
*Assistant Examiner*—Mehdi Rashidian

(57) ABSTRACT

A system and method are provided for contrast-invariant registration of images, the system including a processor, an imaging adapter or a communications adapter for receiving an image data sequence, a user interface adapter for selecting a reference frame from the image sequence or cropping a region of interest (ROI) from the reference frame, a tracking unit for tracking the ROI across the image sequence, and an estimation unit for segmenting the ROI in the reference frame or performing an affine registration for the ROI; and the method including receiving an image sequence, selecting a reference frame from the image sequence, cropping a region of interest (ROI) from the reference frame, tracking the ROI across the image sequence, segmenting the ROI in the reference frame, and performing an affine registration for the ROI.

19 Claims, 6 Drawing Sheets

CONTRAST-INVARIANT REGISTRATION OF CARDIAC AND RENAL MAGNETIC RESONANCE PERFUSION IMAGES

CROSS-REFERENCE TO RELATED APPLICATIONS

This application is a continuation-in-part of co-pending U.S. patent application Ser. No. 09/970,552, filed Oct. 4, 2001 and entitled "System and Method for Segmenting the Left Ventricle in a Cardiac MR Image", which issued as U.S. Pat. No. 6,961,454 on Nov. 1, 2005; and claims the benefit of U.S. Provisional Application Ser. No. 60/553,216 filed Mar. 15, 2004 and entitled "Contrast-Invariant Registration of Cardiac and Renal MR Perfusion Images", the disclosures of which are incorporated herein by reference in their entireties.

BACKGROUND

Dynamic perfusion magnetic resonance imaging (MRI) has demonstrated great potential for diagnosing cardiovascular and renovascular diseases. In dynamic perfusion MRI, the organ under study is scanned rapidly and repeatedly following a bolus injection of a contrast agent. Changes in pixel intensity corresponding to the same tissue across the image sequence provide valuable functional information about the organ being imaged.

Unfortunately, perfusion magnetic resonance (MR) image sequences suffer from motion induced by patient breathing during acquisition. Therefore, registration must be performed on time-series images to ensure the correspondence of anatomical structures in different frames. Due to the vast amounts of data acquired in dynamic perfusion MRI studies, which, on average, include over 100 images per scan, automatic registration is strongly desirable.

Given a sequence of perfusion MR images for the heart or the kidney, it is desirable to solve the registration problem by establishing the appropriate correspondence between every pixel in the region of interest in each frame of the sequence. Unfortunately, this is difficult and standard block matching techniques do not work because the intensity at the same physical location changes across the MR image sequence due to the wash-in and wash-out of the contrast agent. There has been limited work on image registration to address these difficulties. An image registration algorithm that utilizes the maximization of mutual information has been proposed for cardiac MR perfusion data, and a few methods have been proposed for registration of renal MR perfusion images. These methods all require manually drawn contours in one time frame to obtain a mask or a model. This model is then used to propagate the contours to other frames in the image sequence. Thus, what is needed is automatic registration of cardiac and renal MR perfusion images.

SUMMARY

These and other drawbacks and disadvantages of the prior art are addressed by an exemplary system and method for contrast-invariant registration of cardiac and renal magnetic resonance perfusion images.

An exemplary system embodiment for contrast-invariant registration of images includes a processor, an imaging adapter or a communications adapter in signal communication with the processor for receiving an image data sequence, a user interface adapter in signal communication with the processor for selecting a reference frame from the image sequence or cropping a region of interest (ROI) from the reference frame, a tracking unit in signal communication with the processor for tracking the ROI across the image sequence, and an estimation unit in signal communication with the processor for segmenting the ROI in the reference frame or performing an affine registration for the ROI.

A corresponding exemplary method embodiment for contrast-invariant registration of images includes receiving an image sequence, selecting a reference frame from the image sequence, cropping a region of interest (ROI) from the reference frame, tracking the ROI across the image sequence, segmenting the ROI in the reference frame, and performing an affine registration for the ROI.

These and other aspects, features and advantages of the present disclosure will become apparent from the following description of exemplary embodiments, which is to be read in connection with the accompanying drawings.

BRIEF DESCRIPTION OF THE DRAWINGS

The present disclosure teaches a system and method for contrast-invariant registration of cardiac and renal magnetic resonance perfusion images, in which.

DETAILED DESCRIPTION OF PREFERRED EMBODIMENTS

Automatic registration of dynamic MR perfusion images is a challenging task due to the rapid changes of the image contrast caused by the wash-in and wash-out of the contrast agent. Embodiments of the present disclosure use a contrast-invariant similarity metric and a common framework to perform affine registration on both cardiac and renal MR perfusion images. Large-scale translational motion is identified by tracking a selected region of interest with integer pixel shifts, and then the affine transformation of the organ is estimated for each frame. The exemplary algorithm has been tested on real cardiac and renal MR perfusion scans and obtained encouraging registration results.

Figure 1:
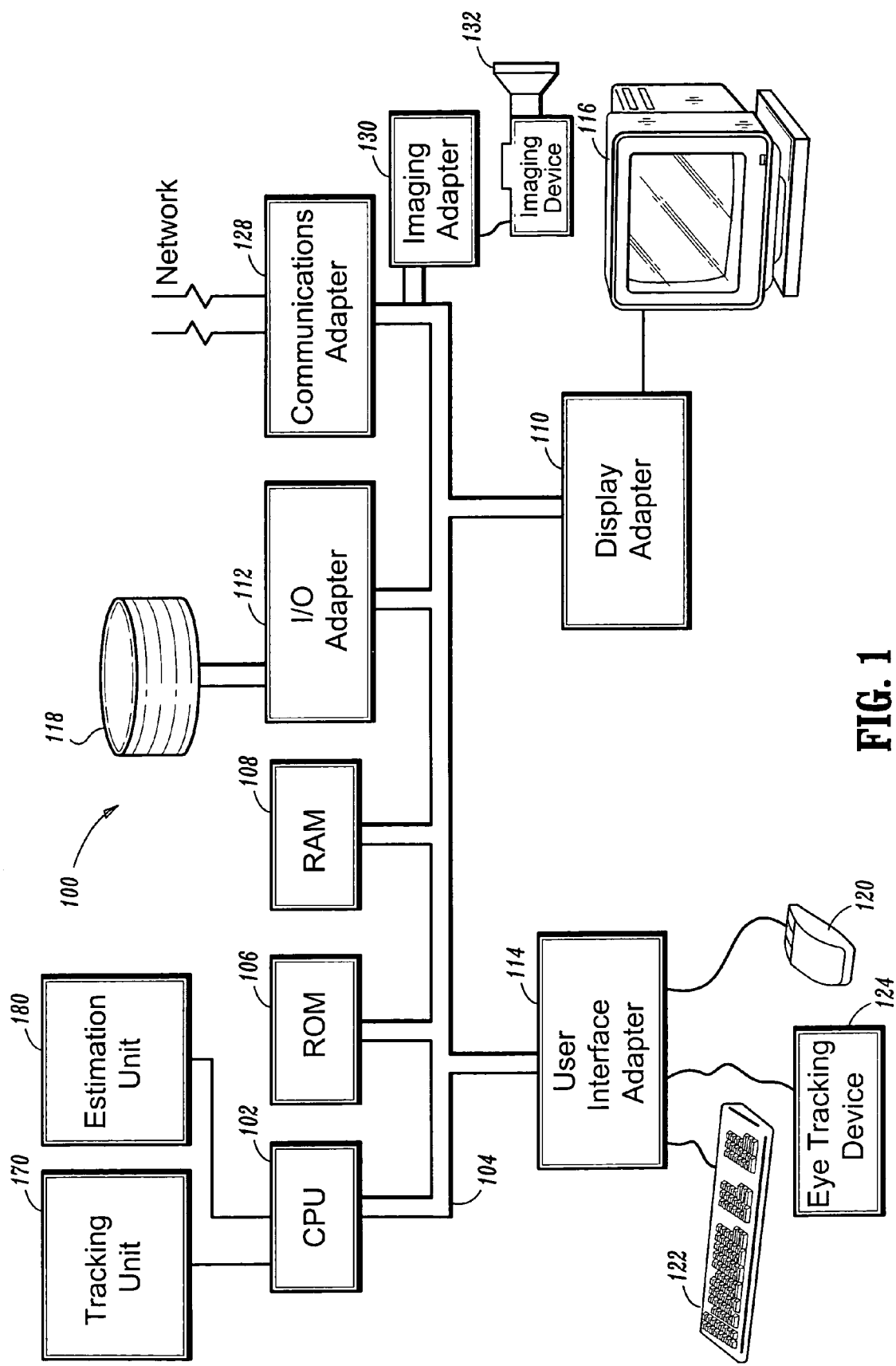
FIG. 1 shows a schematic diagram of a system for contrast-invariant registration of images in accordance with an illustrative embodiment of the present disclosure.

As shown in FIG. 1, a system for contrast-invariant registration of cardiac and renal magnetic resonance perfusion images, according to an illustrative embodiment of the present disclosure, is indicated generally by the reference numeral 100. The system 100 includes at least one processor or central processing unit (CPU) 102 in signal communication with a system bus 104. A read only memory (ROM) 106, a random access memory (RAM) 108, a display adapter 110, an I/O adapter 112, a user interface adapter 114, a communications adapter 128, and an imaging adapter 130 are also in signal communication with the system bus 104. A display unit 116 is in signal communication with the system bus 104 via the display adapter 110. A disk storage unit 118, such as, for example, a magnetic or optical disk storage unit is in signal communication with the system bus 104 via the I/O adapter 112. A mouse 120, a keyboard 122, and an eye tracking device 124 are in signal communication with the system bus 104 via the user interface adapter 114. An imaging device 132 is in signal communication with the system bus 104 via the imaging adapter 130.

A tracking unit 170 and an estimation unit 180 are also included in the system 100 and in signal communication with the CPU 102 and the system bus 104. While the tracking unit 170 and the estimation unit 180 are illustrated as coupled to the at least one processor or CPU 102, these components are preferably embodied in computer program code stored in at least one of the memories 106, 108 and 118, wherein the computer program code is executed by the CPU 102.

Figure 2:
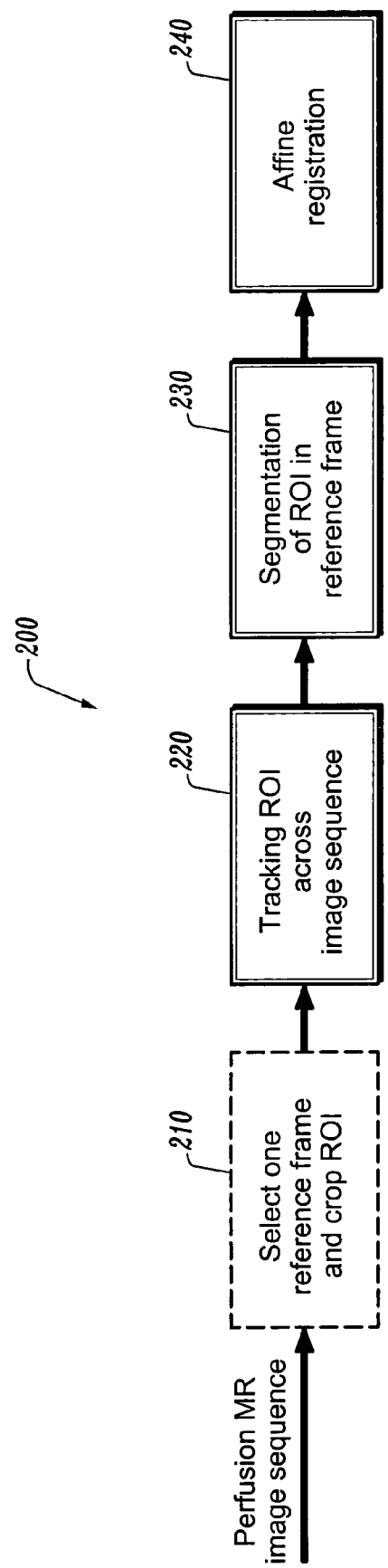
FIG. 2 shows a flow diagram of a method for contrast-invariant registration of images in accordance with an illustrative embodiment of the present disclosure.

Turning to FIG. 2, a method for contrast-invariant registration of cardiac and renal magnetic resonance perfusion images, according to an illustrative embodiment of the present disclosure, is indicated generally by the reference numeral 200. The method 200 includes an optional function block 210 that receives a perfusion MR image sequence, selects one reference frame and crops a region of interest (ROI). The optional function block 210 passes control to a function block 220. The function block 220 tracks the ROI across the image sequence, and passes control to a function block 230. The function block 230, in turn, segments the ROI in the reference frame, and passes control to a function block 240 that performs an affine registration.

Figure 3:
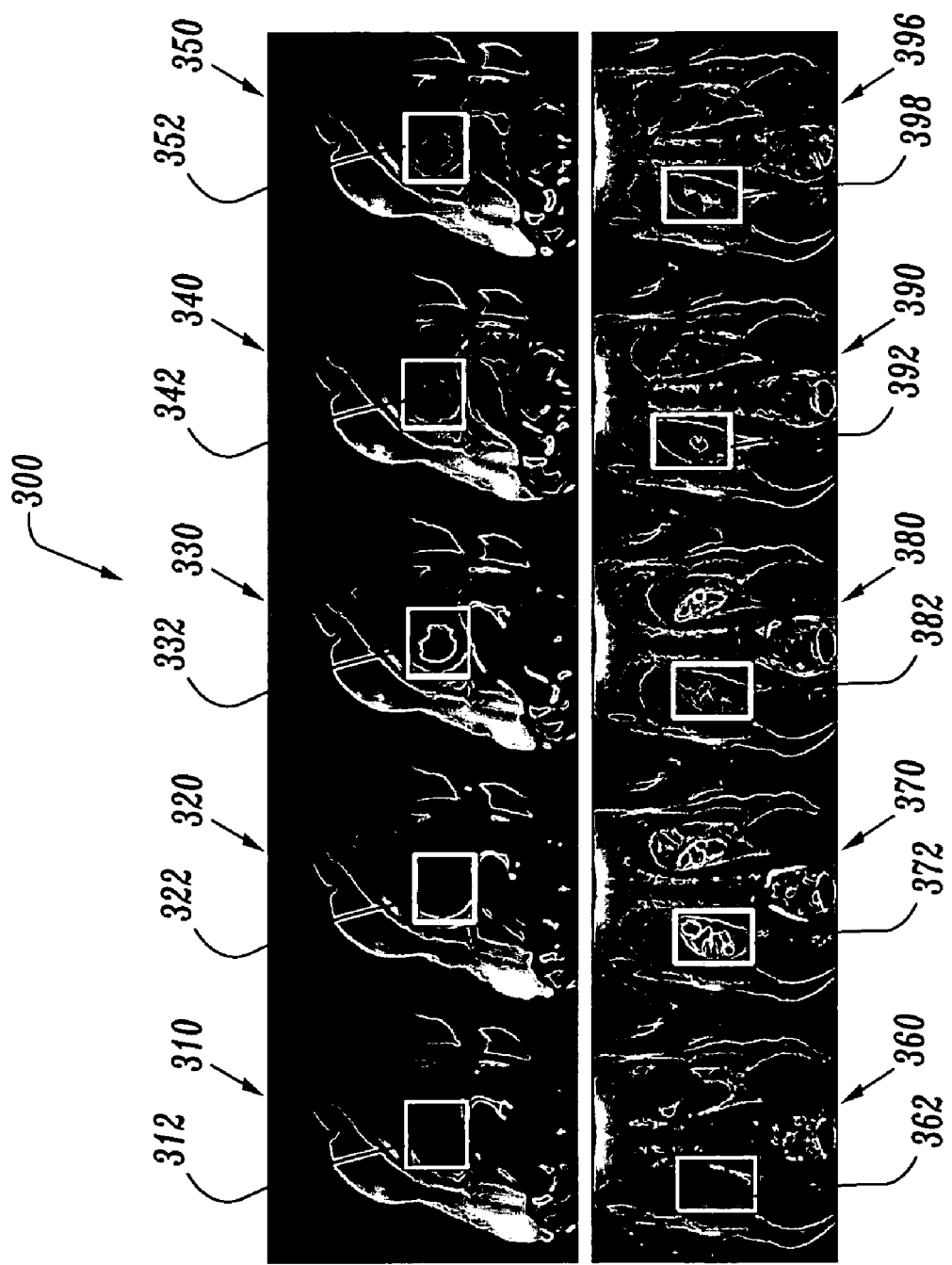
FIG. 3 shows graphical image diagrams for results obtained by tracking the ROI with integer pixel shifts on selected frames from a cardiac (top) and a renal (bottom) MR perfusion image sequence in accordance with an illustrative embodiment of the present disclosure.

Turning now to FIG. 3, selected time-wise ordered frames from perfusion scans with results obtained by tracking the ROI with integer pixel shifts are indicated generally by the reference numeral 300. The frames 310, 320, 330, 340 and 350 are selected from a renal MR perfusion scan, while the frames 360, 370, 380, 390 and 396 are selected from a cardiac MR perfusion scan. In cardiac perfusion, the contrast agent passes through the right ventricle to the left ventricle and then perfuses into the myocardium. Similarly, the intensity of the kidney increases as the contrast agent perfuses into the cortex, the medulla, and other structures of the kidney. Each of the above renal frames includes a bounding box 312, 322, 332, 342 or 352, respectively, while each of the above cardiac frames includes a bounding box 362, 372, 382, 392 and 398, respectively.

Figure 4:
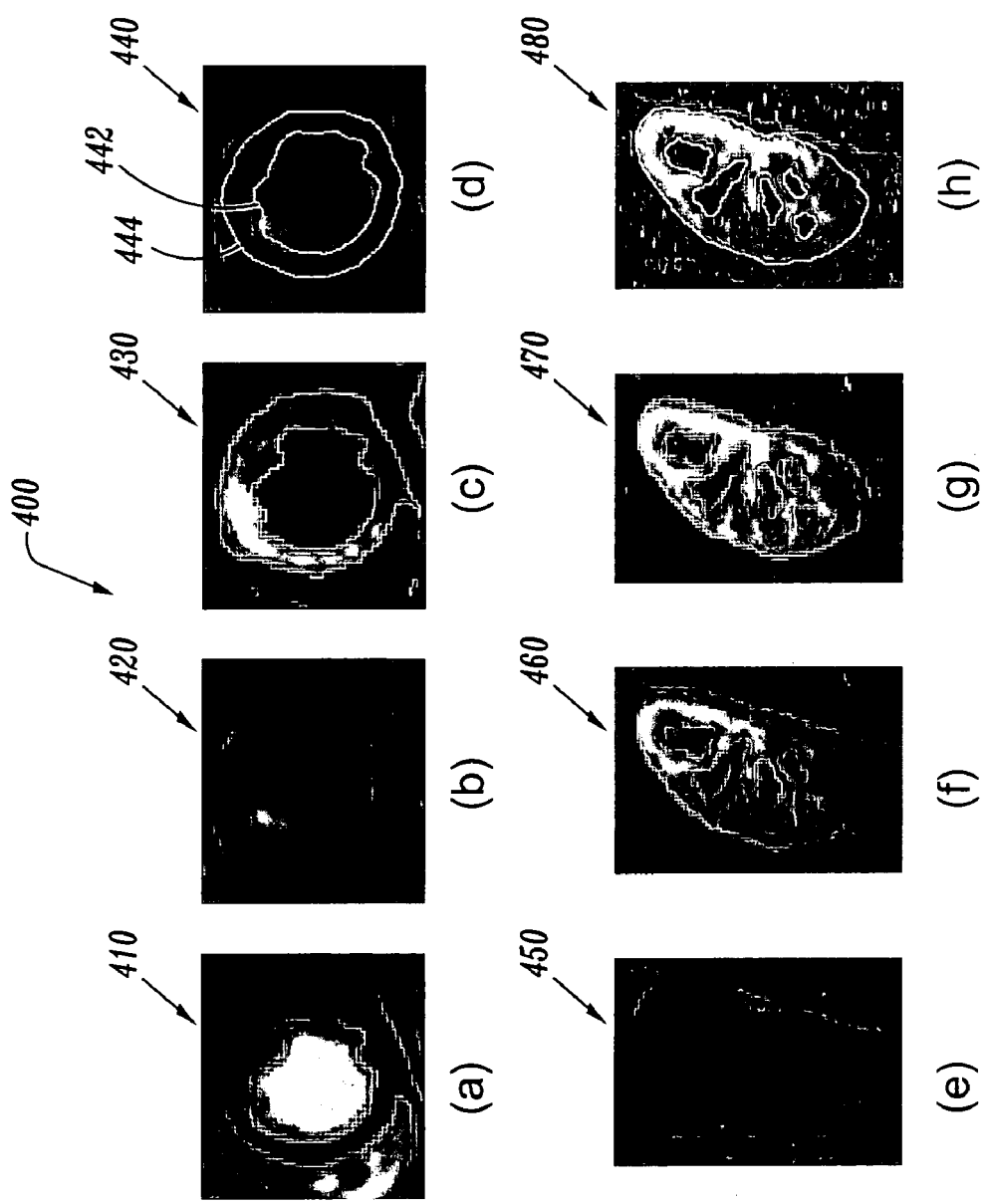
FIG. 4 shows graphical image diagrams for segmentation results of roughly registered images in accordance with an illustrative embodiment of the present disclosure.

As shown in FIG. 4, segmentation results of roughly registered images are indicated generally by the reference numeral 400. Here, an image 430 is obtained by subtracting an image 410 from an image 420. An image 440 includes the detected endocardium 442 and epicardium 444, delineated using bright contours on top of the reference frame. A subtraction between an image 450 and an image 460 results in an enhanced image 470 for the renal MR perfusion scan. The segmentation results are overlaid on top of the reference frame in an image 480.

Figure 5:
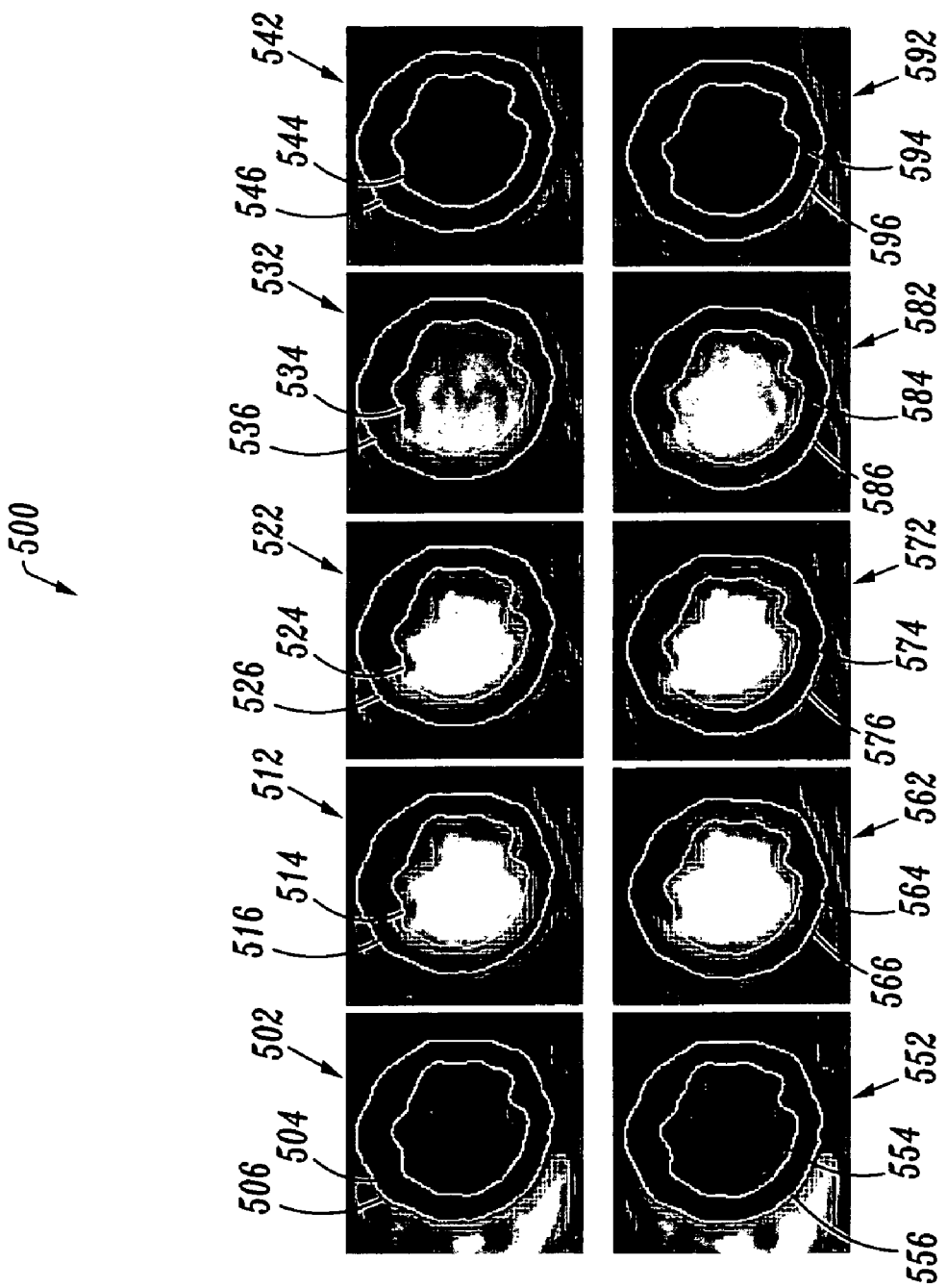
FIG. 5 shows graphical image diagrams of registration results for representative frames from a real patient cardiac MR perfusion scan in accordance with an illustrative embodiment of the present disclosure.

Turning to FIG. 5, registration results for representative image frames from a real patient cardiac MR perfusion scan are indicated generally by the reference numeral 500. Image frames for a real cardiac MR perfusion scan before applying affine registration include the frames 502, 512, 522, 532 and 542, having endocardium contours 504, 514, 524, 534 and 544, respectively, and epicardium contours 506, 516, 526, 536 and 546, respectively. Image frames for a real cardiac MR perfusion scan after applying affine registration include the frames 552, 562, 572, 582 and 592, having endocardium contours 554, 564, 574, 584 and 594, respectively, and epicardium contours 556, 566, 576, 586 and 596, respectively. Thus, the top row shows the segmentation results obtained with the contours overlaid on the registered ROI, and the bottom row shows the transformed contours after applying affine registration.

Figure 6:
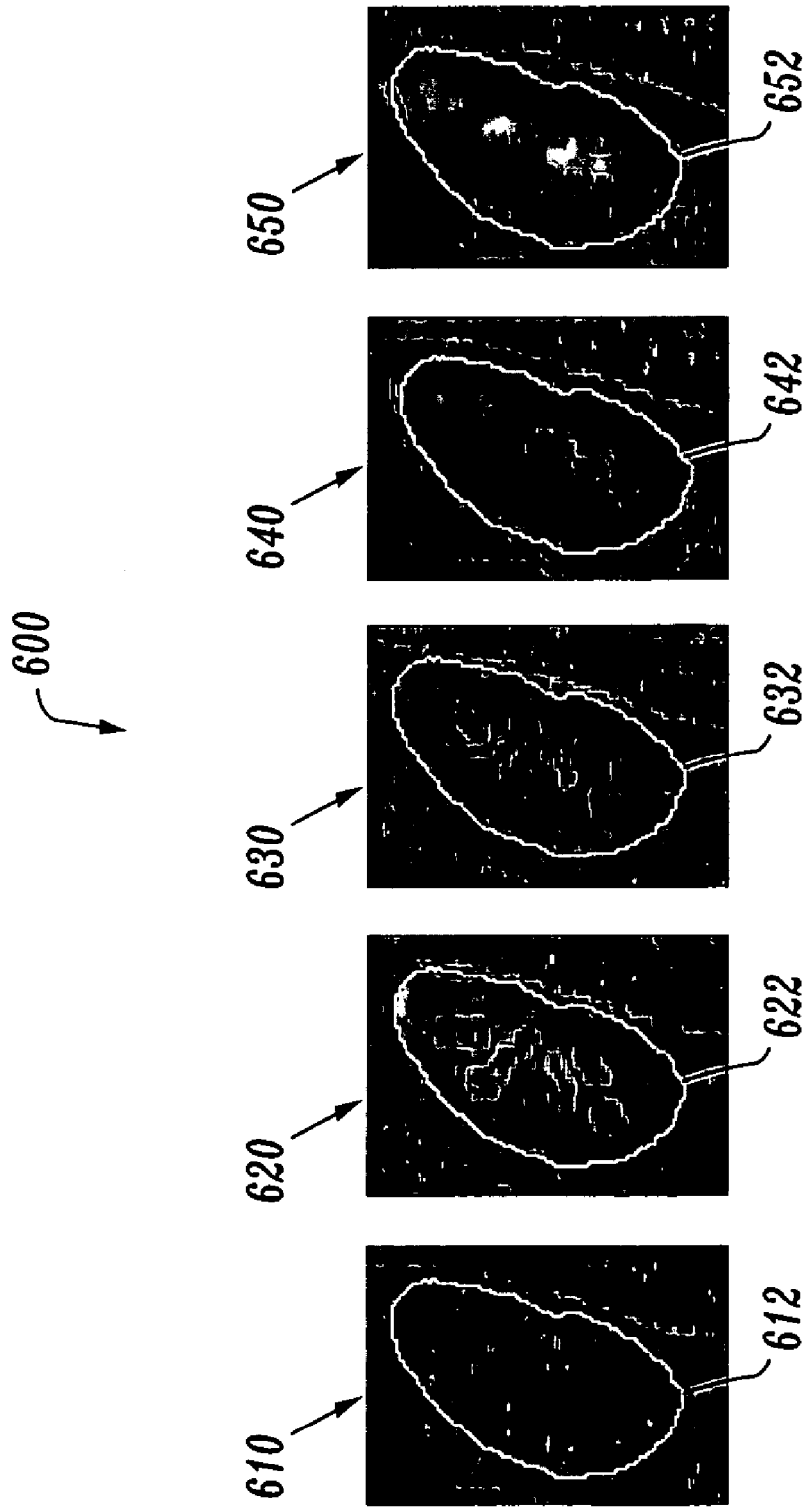
FIG. 6 shows graphical image diagrams of registration results for selected frames from a renal MR perfusion scan in accordance with an illustrative embodiment of the present disclosure.

Turning now to FIG. 6, registration results for selected frames from a renal MR perfusion scan are indicated generally by the reference numeral 600. Here, the frames 610, 620, 630, 640 and 650 are in time-wise order, and include segmentation contours 612, 622, 632, 642 and 652, respectively, which illustrate the performance of the registration algorithm with renal MR perfusion data for a real patient.

In operation, given a sequence of perfusion MR images for the heart or the kidney, an exemplary embodiment approach solves the registration problem by establishing the appropriate correspondence between every pixel in the region of interest in each frame of the sequence. Standard block matching techniques do not work because the intensity at the same physical location changes across the MR image sequence due to the wash-in and wash-out of the contrast agent.

An exemplary embodiment algorithm avoids manually drawn contours and permits the user to crop a rectangular region of interest (ROI). Since translation is the dominant motion caused by breathing, the registration problem is divided into two steps: large translation motion followed by affine transformation. The detailed sequence of steps is as follows.

(1) Choose a reference frame and define a bounding box for the ROI;

(2) Compute the edge map in the bounding box of the reference frame and in the search window of other frames in the MR image sequence;

(3) Determine large-scale translation motion of the ROI by maximizing a contrast invariant similarity metric between the current and the reference frames;

(4) Obtain the contours that delineate the boundaries of the organ in the reference frame through the segmentation of a difference image;

(5) Propagate the segmentation results to other frames by searching for the affine transformations that best match these frames to the reference frame.

Except for the first step, all other steps are automatic. Experimental results with real patient data show that by exploiting the invariance of the similarity metric, this algorithm provides very good registration results.

From the application point of view, it is reasonable to ask the user to select from the sequence of images one that has a good contrast and then crop an ROI in this selected frame. Referring back to FIG. 2, three main stages of the algorithm are tracking the ROI across the image sequence, segmentation of the ROI in the reference frame, and affine registration.

Tracking the ROI across the image sequence is described. Given an ROI in one frame, this stage finds the best match to the selected ROI in other frames. At this stage, it is assumed that the motion is reduced to translation with integer pixel shifts. Tracking the ROI is achieved by simple template matching. The key observation is that the orientations of the edges along tissue boundaries are always parallel across the image sequence, despite the fact that the relative intensities between tissues vary with time. Therefore, the template defined by the orientation of the image gradient is chosen.

In this formulation, the image on which the ROI is manually cropped is called the reference frame. Let $\theta_r(x, y)$ and $M_r(x, y)$ stand for the direction and the magnitude, respectively, of the image gradient at pixel (x, y) in the is reference frame; one can obtain $\theta_r$ and $M_r$ using a Sobel edge detector as known in the art. The set of pixels in the ROI is denoted as $R=\{(x, y)|x_a \leq x \leq x_b, y_a \leq y \leq y_b\}$, where $(x_a, y_a)$ and $(x_b, y_b)$ are the diagonal points that specify the bounding box of the ROI. Let $\theta_c(x, y)$ denote the edge orientation and $M_c(x, y)$ the edge magnitude at pixel (x, y) in the current frame. For each offset pair (dx, dy), the angle difference $\Delta\theta(x, y; dx, dy)$ and a weight function w(x, y; dx, dy) are defined by:

$$\Delta\theta(x, y; dx, dy) = \theta_c(x+dx, y+dy) - \theta_r(x, y) \quad (1)$$

$$w(x, y; dx, dy) = \frac{M_c(x+dx, y+dy)M_r(x, y)}{\sum_{(x,y)\in R} M_c(x+dx, y+dy)M_r(x, y)} \quad (2)$$

A similarity metric is introduced:

$$S(dx, dy) = \sum_{(x,y)\in R} w(x, y; dx, dy)\cos(2\Delta\theta(x, y; dx, dy)) \quad (3)$$

Note that S(dx, dy) is the weighted average of the values of $\cos(2\Delta\theta)$ over the ROI, and its value lies in the interval of [−1, 1]. The cosine of the double angle is used to handle contrast inversions that commonly occur in perfusion studies. For instance, in a renal MR perfusion scan, referring back to the first image 360 in the bottom row of FIG. 3, the kidney is relatively darker compared to the surrounding tissues before the wash-in of the contrast agent. It becomes relatively brighter after the wash-in of the contrast agent as shown in the second image 370 in the bottom row of FIG. 3. In addition, the weight function is chosen as the normalized product of the edge magnitudes because it is desirable for the ROI to be attracted to strong edges in the current frame that are mostly parallel to the strong edges in the reference frame. The exemplary similarity metric is invariant to rapidly changing image contrast, in the sense that its value is insensitive to changes in the contrast as long as the edge orientations are nearly parallel to those of the template. The integer shifts (dx*, dy*) that maximize S are determined by exploring all possible solutions (dx, dy) over a reasonable search space. It is important to point out that the value of S(dx*, dy*) also plays a role as a confidence measure. To improve the robustness of the algorithm, both the previous frame and the reference frame are used as templates. The algorithm then chooses the match with maximum similarity metric.

Referring back to FIG. 3, selected frames from a renal (top row) and a cardiac (bottom row) MR perfusion scan are displayed, respectively. In cardiac perfusion, the contrast agent passes through the right ventricle to the left ventricle and then perfuses into the myocardium. Similarly, the intensity of the kidney increases as the contrast agent perfuses into the cortex, the medulla, and other structures of the kidney. To illustrate the performance of the exemplary tracking algorithm, the bounding box of the ROI is shifted to the best match location in each frame of FIG. 3. Despite the rapidly changing image contrast and the fact that translational motion between two adjacent frames can be considerably large, the algorithm reliably tracks the selected ROI across the image sequence for both cardiac and renal perfusion studies, with minor tracking error in frames that lack strong edges. To further improve the accuracy of the registration results, the local affine transformation of the heart or kidney is estimated by incorporating the knowledge of the contours delineating organ boundaries in the reference frame.

Segmentation of the ROI is now described. This stage identifies the boundaries of the organ in the reference frame, based on a roughly registered ROI sequence resulting from the previous description. It has been demonstrated that myocardial boundaries can be detected by segmenting a subtraction image, in which the myocardium is accentuated. Referring back to FIG. 4, the image 430 displays the image obtained by subtracting the image 410 from the image 420. Detecting the boundaries of the left ventricle becomes a less challenging problem, to many available segmentation algorithms as known in the art may be applied. An energy minimization approach is taken and a customized energy functional is provided to address application-specific details. To take into account the anatomical constraint that the distance between the endocardium and the epicardium is relatively constant, the idea of coupled propagation of two cardiac contours is used, as known in the art. Since the emphasis of the present disclosure is placed on registration, the segmentation results are presented without further explanation. The detected endocardium and epicardium are delineated respectively using bright contours on top of the reference frame, as shown in 440 of FIG. 4. Although this is an approximate segmentation, it provides enough shape priors to refine the template for affine registration.

Similar to the case of cardiac MR perfusion data, the subtraction between images 450 and 460 of FIG. 4 results in an enhanced image 470 for the renal MR perfusion scan. The level set method as known in the art is applied to extract the renal cortex. This is an energy minimization based segmentation method. It assumes that the image is formed by two regions of approximately piecewise constant intensities of distinct values. It can be seen in 470 of FIG. 4 that the assumption is valid. The image contains a bright object to be detected in a dark background. The segmentation results are overlaid on top of the reference frame in the image 480 of FIG. 4. As shown, the outer boundary of the kidney is well delineated. These results demonstrate that the boundaries of the organ in the reference frame, whether it be a heart or kidney, can be identified.

Affine registration is now described. Integer pixel shifts of the ROI have been compensated for, and the contours that delineate the boundaries of the organ in the reference frame have been obtained. Next, the segmentation results are propagated to other frames by estimating the affine transformation of the organ in each frame.

The affine transformation includes translation, rotation, scaling and shearing. In 2D, the affine transformation between (x, y) and (x', y') is given by $$\begin{bmatrix} x' \\ y' \end{bmatrix} = A \begin{bmatrix} x \\ y \end{bmatrix} + t, \quad (4)$$

where A is a 2×2 invertible matrix that defines rotation, shear, and scale, and t is a 2×1 translation vector.

The segmentation results obtained in the previous step make it possible to refine the template by ignoring irrelevant edge information. Let $L \subset R$ denote the set of pixels in the ROI corresponding to pixels lying on the boundaries of the organ and their nearest neighbors under a second order neighborhood system. Let $\theta'_c(x, y; A, t)$ and $M'_c(x, y; A, t)$ denote the corresponding direction and magnitude of the image gradient in the current frame under the affine transformation defined by A and t. The goal of the affine registration is to find the affine transformation (A, t) that maximizes the following similarity metric for the current image $$S'(A, t) = \sum_{(x,y)\in L} w'(x, y; A, t)\cos(2\Delta\theta'(x, y; A, t)), \quad (5)$$

where $\Delta\theta'(x, y; A, t)$ and $w'(x, y; A, t)$ are computed respectively by $$\Delta\theta'(x, y; A, t) = \theta'_c(x, y; A, t) - \theta_r(x, y), \quad (6)$$

$$w'(x, y; A, t) = \frac{M_c(x, y; A, t)M_r(x, y)}{\sum_{(x,y)\in L} M_c(x, y; A, t)M_r(x, y)}. \quad (7)$$

In the special case where the motion of the organ is highly constrained and approximately rigid, the number of degrees of freedom in the affine transform can be reduced by restricting the motion to rotation and translation. In experiments, the following measures were adopted: (1) keep the scaling fixed and let the rotation vary between −5 to 5 degrees in 1 degree steps; (2) the translation along either dimension is constrained between −2 to 2 pixels; (3) construct a bank of templates for each combination of rotation and translation; and (4) search for the best template that results in the largest similarity metric between the current frame and the reference frame, over the constrained parameter space. This algorithm is fast and insensitive to noise. The algorithm can be extended to maximizing S'(A, t) under affine transformation through a gradient descent method, as known in the art, in an alternate embodiment.

The exemplary algorithm has been tested on 15 cardiac and 12 renal MR perfusion datasets of real patients. Each dataset contains 3 or 4 slices. The images were acquired on Siemens Sonata MR scanners following bolus injection of Gd-DTPA contrast agent. In most cases, the image matrix is 256×256 pixels. The number of frames in each image sequence ranges from 50 to 350.

For all of the data sets in this study, the registration results were qualitatively validated with visual analysis by displaying the registered image sequence in a movie mode. Using the present ROI tracking algorithm, it is able to track the ROI reliably in all the sequences robustly, with a maximum tracking error of less than 2 pixels in both directions. In addition, the experimental results show that affine registration improves the accuracy of the registration greatly. Referring back to FIG. 5, the results obtained before and after applying affine registration are compared for a real cardiac MR perfusion scan. As shown, the contours in the top row of images, before affine registration, do not lie exactly at the boundaries of the left ventricle. This is easily seen at the bottom left of each image where the edge information is relatively strong. On the other hand, the contours in the bottom row of images, after affine registration, delineate well the boundaries of the left ventricle. In particular, the accuracy of the estimated rotation can be visually validated by looking at the papillary muscle at the bottom of each image, for example.

Referring back to FIG. 6, the performance of the registration algorithm with renal MR perfusion data is illustrated with respect to the results for a real patient. The registration results have been validated quantitatively for a renal perfusion MR scan of 150 images, by comparing the estimated translation vector at each frame with a "gold standard", i.e., pixel shifts obtained manually. The error size is less than one pixel in each direction for more than 95% of the frames. These results strongly suggest that the motion caused by breathing can be successfully compensated using the registration algorithm presented herein.

The exemplary algorithm presents a common framework for the registration of dynamic cardiac and renal MR perfusion images. The algorithm exploits image features that are invariant to a rapidly changing contrast and utilizes image segmentation results for the construction of templates. Encouraging registration results have been obtained with real patient datasets. In alternate embodiments, different anatomical structures may be segmented within the ROI based on their distinct dynamics of the first-pass signal, i.e., the pixel intensity-time curve as known in the art.

In alternate embodiments of the apparatus 100, some or all of the computer program code may be stored in registers located on the processor chip 102. In addition, various alternate configurations and implementations of the tracking unit 170 and the estimation unit 180 may be made, as well as of the other elements of the system 100.

It is to be understood that the teachings of the present disclosure may be implemented in various forms of hardware, software, firmware, special purpose processors, or combinations thereof. Most preferably, the teachings of the present disclosure are implemented as a combination of hardware and software.

Moreover, the software is preferably implemented as an application program tangibly embodied on a program storage unit. The application program may be uploaded to, and executed by, a machine comprising any suitable architecture. Preferably, the machine is implemented on a computer platform having hardware such as one or more central processing units (CPU), a random access memory (RAM), and input/output (I/O) interfaces.

The computer platform may also include an operating system and microinstruction code. The various processes and functions described herein may be either part of the microinstruction code or part of the application program, or any combination thereof, which may be executed by a CPU. In addition, various other peripheral units may be connected to the computer platform such as an additional data storage unit and a printing unit.

It is to be further understood that, because some of the constituent system components and methods depicted in the accompanying drawings are preferably implemented in software, the actual connections between the system components or the process function blocks may differ depending upon the manner in which the present disclosure is programmed. Given the teachings herein, one of ordinary skill in the pertinent art will be able to contemplate these and similar implementations or configurations of the present disclosure.

Although the illustrative embodiments have been described herein with reference to the accompanying drawings, it is to be understood that the present disclosure is not limited to those precise embodiments, and that various changes and modifications may be effected therein by one of ordinary skill in the pertinent art without departing from the scope or spirit of the present disclosure. All such changes and modifications are intended to be included within the scope of the present disclosure as set forth in the appended claims.

What is claimed is:

1. A computer implemented method for contrast-invariant registration of images, the method comprising:
   (a) receiving an image sequence of frames;
   (b) selecting a reference frame from the image sequence of frames;

(c) defining a bounding box for a region of interest (ROI) about an object of interest in the reference frame;

(d) determining a large-scale translation motion of the ROI with respect to each of the other frames in the image sequence;

(e) determining contours that delineate boundaries of the object of interest in the reference frame; and (f) propagating the contours to the other frames by finding an affine transformation that best matches a contour in each of the other frames to the contour in the reference frame, wherein steps (a), (d) (e), and (f) are performed by a computer processor.

2. A method as defined in claim 1, further comprising computing an edge map in the bounding box of the reference frame and in the bounding box of other frames in the image sequence.

3. A method as defined in claim 2, wherein large-scale translational motion is determined by maximizing a contrast invariant similarity metric between each of the other frames and the reference frame.

4. A method as defined in claim 1, wherein said contours are determined through the segmentation of a difference image.

5. A method as defined in claim 1, further comprising keeping the scaling of the ROI fixed and varying the rotation of the ROI between about −5 to about 5 degrees in about 1 degree steps.

6. A method as defined in claim 1, further comprising constraining the translation of the ROI along either dimension between about −2 to about 2 pixels.

7. A method as defined in claim 1, further comprising constructing a bank of templates for each combination of rotation and translation of the ROI.

8. A method as defined in claim 1, further comprising searching for the best template that results in the largest similarity metric between the current frame and the reference frame, over a constrained parameter space wherein motion of the object of interest is rigid.

9. A method as defined in claim 1 wherein the image sequence is a perfusion magnetic resonance (MR) image sequence.

10. A non-transitory computer-readable medium, tangibly embodying a computer program to perform program steps for contrast-invariant registration of images, the program steps comprising:

receiving an image sequence of frames;

selecting a reference frame from the image sequence of frames;

defining a bounding box for a region of interest (ROI) about an object of interest in the reference frame;

determining a large-scale translation motion of the ROI with respect to each of the other frames in the image sequence;

determining contours that delineate boundaries of the object of interest in the reference frame; and propagating the contours to the other frames by finding an affine transformation that best matches a contour in each of the other frames to the contour in the reference frame.

11. A non-transitory computer-readable medium as defined in claim 10, the program steps further comprising computing an edge map in the bounding box of the reference frame and in the bounding box of other frames in the image sequence.

12. A non-transitory computer-readable medium as defined in claim 10 wherein large-scale translational motion is determined by maximizing a contrast invariant similarity metric between each of the other frames and the reference frame.

13. A non-transitory computer-readable medium as defined in claim 10, wherein said contours are determined through the segmentation of a difference image.

14. A method as defined in claim 2, wherein computing an edge map comprises computing a direction $\theta_r(x, y)$ and magnitude $M_r(x, y)$ respectively, of the image gradient at pixel (x, y) in the reference frame, and computing a direction $\theta_c(x, y)$ and magnitude $M_c(x, y)$, respectively, of the image gradient at pixel (x, y) in another frame c.

15. A method as defined in claim 14, wherein said contrast invariant similarity metric is defined by $$S(dx, dy) = \sum_{(x,y) \in R} w(x, y, dx, dy) \cos(2\Delta\theta(x, y, dx, dy))$$

wherein, for each offset pair (dx, dy), an angle difference $\Delta\theta(x, y, dx, dy)$ and a weight function w(x, y, dx, dy) are defined by:

$$\Delta\theta(x, y, dx, dy) = \theta_c(x+dx, y+dy) - \theta_r(x, y),$$

and $$w(x, y, dx, dy) = \frac{M_c(x+dx, y+dy)M_r(x, y)}{\sum_{(x,y) \in R} M_c(x+dx, y+dy)M_r(x, y)},$$

wherein a set of pixels in the ROI are defined by R = {(x, y)|$x_a \leq x \leq x_b$, $y_a \leq y \leq y_b$} and wherein $(x_a, y_a),(x_b, y_b)$ are diagonal points that specify the bounding box of the ROI.

16. A method as defined in claim 14, wherein finding an affine transformation that best matches a contour in each of the other frames to the contour in the reference frame comprises finding an affine transformation (A, t), wherein A is a 2×2 invertible matrix that defines rotation, shear, and scale, and t is a 2×1 translation vector, that maximizes a similarity matrix S'-(A, t) for a current frame where $$S'(A, t) = \sum_{(x,y) \in L} w'(x, y, A, t) \cos(2\Delta\theta'(x, y, A, t))$$

wherein L ⊂ ROI is a set of pixels lying on boundaries of the object of interest and their nearest neighbors under a second order neighborhood system, $\Delta\theta'(x, y, A, t) = \theta_c'(x, y, A, t) - \theta_r(x, y)$ wherein $\theta_c'(x, y, A, t)$ is the direction of the image gradient in another frame c under the affine transformation, $$w'(x, y, A, t) = \frac{M_c'(x, y, A, t)M_r(x, y)}{\sum_{(x,y) \in L} M_c'(x, y, A, t)M_r(x, y)},$$

wherein w'(x, y, A, t) is the weight function and $M_c'(x, y, A, t)$ is the magnitude of the image gradient in the current frame under the affine transformation, wherein said affine transformation transforms a pixel (x, y) as $$\begin{bmatrix} x' \\ y' \end{bmatrix} = A \begin{bmatrix} x \\ y \end{bmatrix} + t.$$

17. A non transitory computer-readable medium as defined in claim 11, wherein computing an edge map comprises computing a direction $\theta_r(x, y)$ and magnitude $M_r(x, y)$ respectively, of the image gradient at pixel $(x, y)$ in the reference frame, and computing a direction $\theta_c(x, y)$ and magnitude $M_c(x, y)$, respectively, of the image gradient at pixel $(x, y)$ in another frame c.

18. A non transitory computer-readable medium as defined in claim 17, wherein said contrast invariant similarity metric $S'(dx, dy)$ is defined by $$S(dx, dy) = \sum_{(x,y) \in R} w(x, y, dx, dy) \cos(2\Delta\theta(x, y, dx, dy))$$

wherein, for each offset pair $(dx, dy)$, an angle difference $\Delta\theta(x, y, dx, dy)$ and a weight function $w(x, y, dx, dy)$ are defined by:

$$\Delta\theta(x, y, dx, dy) = \theta_c(x+dx, y+dy) - \theta_r(x, y),$$

and $$w(x, y, dx, dy) = \frac{M_c(x+dx, y+dy) M_r(x, y)}{\sum_{(x,y) \in R} M_c(x+dx, y+dy) M_r(x, y)},$$

wherein a set of pixels in the ROI are defined by $R = \{(x, y) | x_a \leq x \leq x_b, y_a \leq y \leq y_b\}$ and wherein $(x_a, y_a), (x_b, y_b)$ are diagonal points that specify the bounding box of the ROI.

19. A non transitory computer-readable medium as defined in claim 17, wherein finding an affine transformation that best matches a contour in each of the other frames to the contour in the reference frame comprises finding an affine transformation $(A, t)$, wherein A is a 2×2 invertible matrix that defines rotation, shear, and scale, and t is a 2×1 translation vector, that maximizes a similarity matrix $S'$-$(A, t)$ for a current frame where $$S'(A, t) = \sum_{(x,y) \in L} w'(x, y, A, t) \cos(2\Delta\theta'(x, y, A, t))$$

wherein $L \subset ROI$ is a set of pixels lying on boundaries of the object of interest and their nearest neighbors under a second order neighborhood system, $\Delta\theta'(x, y, A, t) = \theta_c'(x, y, A, t) - \theta_r(x, y)$ wherein $w'(x, y, A, t)$ is the weight function and $\theta_c'(x, y, A, t)$ is the direction of the image gradient in another frame c under the affine transformation, $$w'(x, y, A, t) = \frac{M_c'(x, y, A, t) M_r(x, y)}{\sum_{(x,y) \in L} M_c'(x, y, A, t) M_r(x, y)},$$

wherein $M_c'(x, y, A, t)$ is the magnitude of the image gradient in the current frame under the affine transformation, wherein said affine transformation transforms a pixel $(x, y)$ as $$\begin{bmatrix} x' \\ y' \end{bmatrix} = A \begin{bmatrix} x \\ y \end{bmatrix} + t.$$

* * * * *